United States Patent
Humphries et al.

(10) Patent No.: US 9,155,726 B2
(45) Date of Patent: *Oct. 13, 2015

(54) METHOD OF TREATMENT USING CHECKPOINT KINASE 1 INHIBITORS

(71) Applicant: ARRAY BIOPHARMA INC., Boulder, CO (US)

(72) Inventors: Michael J. Humphries, Boulder, CO (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,091

(22) Filed: Jun. 7, 2013

(65) Prior Publication Data

US 2014/0045782 A1  Feb. 13, 2014

Related U.S. Application Data

(63) Continuation of application No. 12/757,954, filed on Apr. 9, 2010, now Pat. No. 8,481,557.

(60) Provisional application No. 61/168,564, filed on Apr. 11, 2009.

(51) Int. Cl.

| | |
|---|---|
| *A61K 31/4545* | (2006.01) |
| *A61K 31/4745* | (2006.01) |
| *A61K 31/513* | (2006.01) |
| *A61K 31/519* | (2006.01) |
| *A61K 31/664* | (2006.01) |
| *A61K 31/704* | (2006.01) |
| *A61K 31/7068* | (2006.01) |
| *A61K 31/7076* | (2006.01) |
| *A61K 33/24* | (2006.01) |
| *A61K 45/06* | (2006.01) |
| *A61K 31/4375* | (2006.01) |
| *A61K 31/437* | (2006.01) |

(52) U.S. Cl.
CPC .......... *A61K 31/437* (2013.01); *A61K 31/4375* (2013.01); *A61K 31/4545* (2013.01); *A61K 31/4745* (2013.01); *A61K 31/513* (2013.01); *A61K 31/519* (2013.01); *A61K 31/664* (2013.01); *A61K 31/704* (2013.01); *A61K 31/7068* (2013.01); *A61K 31/7076* (2013.01); *A61K 33/24* (2013.01); *A61K 45/06* (2013.01)

(58) Field of Classification Search
CPC .......... A61K 31/437; A61K 31/4545; A61K 35/4745; A61K 31/513; A61K 31/519; A61K 31/664; A61K 31/704; A61K 31/7068; A61K 31/7076; A61K 33/24; A61K 45/06; A61K 331/4375

See application file for complete search history.

(56) References Cited

U.S. PATENT DOCUMENTS

| | | |
|---|---|---|
| 8,178,131 B2 | 5/2012 | Huerou et al. |
| 8,372,842 B2 | 2/2013 | Blake et al. |
| 8,481,557 B2 | 7/2013 | Humphries et al. |
| 8,545,897 B2 | 10/2013 | Huerou et al. |
| 8,758,830 B2 | 6/2014 | Huerou et al. |
| 2010/0280043 A1 | 11/2010 | Blake et al. |
| 2010/0324041 A1 | 12/2010 | Blake et al. |
| 2013/0231301 A1 | 9/2013 | Davies et al. |
| 2014/0221370 A1 | 8/2014 | Blake et al. |
| 2014/0243520 A1 | 8/2014 | Huerou et al. |

FOREIGN PATENT DOCUMENTS

| | | |
|---|---|---|
| EP | 2079203 A1 | 7/2009 |
| WO | WO 03/028724 | 4/2003 |
| WO | WO 2005/027907 A1 | 3/2005 |
| WO | WO 2005/066163 | 7/2005 |
| WO | WO 2005/103036 | 11/2005 |
| WO | WO 2006/046023 | 5/2006 |
| WO | WO 2006/106326 | 10/2006 |
| WO | WO 2006/120573 | 11/2006 |
| WO | WO 2007/090493 | 8/2007 |
| WO | WO 2007/090494 | 8/2007 |
| WO | WO 2007/113671 | 10/2007 |
| WO | WO 2008/012635 | 1/2008 |
| WO | WO 2008/063558 | 5/2008 |
| WO | WO 2009/004329 | 1/2009 |
| WO | WO 2009/140320 | 11/2009 |
| WO | WO 2010/118390 | 10/2010 |
| WO | WO 2012/074754 | 6/2012 |

OTHER PUBLICATIONS

Ahn et al., "The Chk2 Protein Kinase", DNA Repair, 3, pp. 1039-1047, (2004).

Bartek et al., "CHK2 Kinase—A Busy Messenger", Nature Reviews Molecular Cell Biology, vol. 2 (12), pp. 877-886, (2001).

Burgess et al., "Discovery of pyrazinyl ureas as inhibitors of cell-cycle checkpoint kinase Chk1", AACR Special Conference, Cell Cycle and Cancer: Pathways and Therapies, 22 pages, Dec. 1, 2004.

Davies et al., "Single-agent Chk1 inhibition is anti-proliferative in leukemia cells in vitro and in vivo", Abstract #3874, American Association of Cancer Research 101st Annual Meeting, 1 page, Apr. 20, 2010.

Davies et al., "Chk1 inhibition and Wee1 inhibition combine synergistically to inhibit cellular proliferation", Abstract #2939, American Association of Cancer Research 102nd Annual Meeting, 1 page, Apr. 5, 2011.

Davies et al., "Single-Agent Inhibition of Chk1 Is Antiproliferative in Human Cancer Cell Lines In Vitro and Inhibits Tumor Xenograft Growth In Vivo", *Oncology Research*. vol. 19, 349-363 (2011).

Humphries et al., "Schedule-dependence and extended target-coverage of selective Chk1 inhibitors enhances the anti-tumor activity of chemotherapy in vivo", Abstract #4599, American Association of Cancer Research 100$^{th}$ Annual Meeting, 1 page, Apr. 21, 2009.

(Continued)

*Primary Examiner* — Renee Claytor

(74) *Attorney, Agent, or Firm* — Viksnins Harris & Padys PLLP

(57) ABSTRACT

Methods of treating cancer by administering a DNA damaging agent and a CHK1 Inhibitor on a dosing regimen are provided.

28 Claims, 13 Drawing Sheets

(56) References Cited

OTHER PUBLICATIONS

Humphries et al., "Extended target-coverage by selective Chk1 inhibitors enhances pharmacodynamic inhibition of Chk1 signaling and anti-tumor activity in vivo", Abstract #B254, 2009 AACR-NCI-EORTC International Conference Molecular Targets and Cancer Therapeutics, 1 page, Nov. 17, 2009.

Humphries, "Targeting Checkpoint Kinase 1: A study in the application of preclinical data to inform clinical strategy", 2nd Annual Cancer Targets & Therapeutics Conference, 21 pages, Oct. 21, 2010.

Humphries, "Preclinical characterization of ARRY-575: A potent, selective, and orally bio-available small molecule inhibitor of Chk1", International Symposium on Targeted Anticancer Therapies, 11 pages, Mar. 11, 2011.

Janetka et al., Inhibitors of Checkpoint Kinases: From Discovery to the Clinic:, Drug Discovery & Development, vol. 10, No. 4, pp. 473-486, (2007).

Kesicki et al., "Discovery of pyrazinyl ureas as inhibitors of cell-cycle checkpoint kinase Chk1", The 228th ACS National Meeting, 1 page, Aug. 23, 2004.

Matthews et al., "Pharmacological abrogation of S-phase checkpoint enhances the anti-tumor activity of gemcitabine in vivo", *Cell Cyclr.* 6(1), 104-110 (2007).

Parsels et al., "Gemcitabine sensitization by checkpoint kinase 1 inhibition of Rad51 DNA damage response in pancreatic cancer cells", *Mol. Cancer Ther*. 8(1), 45-54 (2009).

Patent Cooperation Treaty, International Search Report and Written Opinion for PCT/US2010/030634, 11 pages, Sep. 9, 2010.

Pommier et al., "Targeting Chk2 Kinase: Molecular Interaction Maps and Therapeutic Rationale", Current Pharmaceutical Design, vol. 11, No. 22, pp. 2855-2872, (2005).

Tse et al., "Targeting Checkpoint Kinase 1 in Cancer Therapeutics", *Clin. Cancer Res*. 13 (7), pp. 1955-1960, (2007).

Tse et al., "CHIR-124, a Novel Potent Inhibitor of Chk1, Potentiates the Cytotoxicity of Topoisomerase I Poisons In vitro and In vivo", *Clin. Cancer Res.*, 13 (2), pp. 591-602, 2007.

Tse, Archie N., et al. EORTC 2008. "Phase 1 Study of XL844, a Novel Chk1 and Chk2 Kinase Inhibitor, in Combination with Gemcitabine in Subjects with Advanced Malignancies." http://www.exelixis.com/eortc/posters/EORTC08_395_XL844-002.pdf.

Von Carlowitz et al., "Characterization of a Novel, Oral Chk1 Inhibitor", Abstract #1803, American Association of Cancer Research 100th Annual Meeting, 1 page, Apr. 21, 2009.

Zabludoff et al., "AZD7762, a novel cycle checkpoint kinase, drives checkpoint abrogation and potentiates DNA-targeted therapies", *Mol. Cancer Ther*. 7(9), 2955-2966 (2008).

METHOD OF TREATMENT USING CHECKPOINT KINASE 1 INHIBITORS

RELATED APPLICATIONS

This application is a Continuation Application of U.S. application Ser. No. 12/757,954 filed on Apr. 9, 2010, which claims benefit of priority under 35 U.S.C. §119(e) to U.S. Provisional Patent Application Ser. No. 61/168,564, filed Apr. 11, 2009. The entirety of all Applications listed above are incorporated herein by reference.

BACKGROUND OF THE INVENTION

1. Field of the Invention

The present invention relates to a method for increasing effectiveness of a chemotherapeutic or decreasing the resistance to a DNA damaging agent by inhibiting checkpoint kinase 1 on a specific dosing schedule.

2. Description of the State of Art

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." *Clin. Cancer Res.* 13(7) (2007) 1955-1960). It has been observed that many tumors are deficient in the G1 DNA damage checkpoint pathway, resulting in the reliance on S and G2 checkpoints to repair DNA damage and survive. (Janetka, James W., et al., "Inhibitors of checkpoint kinases: From discovery to the clinic." *Drug Discovery & Development* Vol. 10, No. 4 (2007) 473-486). The S and G2 checkpoints are regulated by CHK1 Inhibition of CHK1 has been shown to cancel the S and G2 checkpoints, thereby impairing DNA repair and resulting in increased tumor cell death. However, non-cancerous cells have a functioning G1 checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al., "The Chk2 protein kinase." *DNA Repair* 3 (2004) 1039-1047). CHK2 is activated in response to genotoxic insults and propagates the checkpoint signal along several pathways, which eventually causes cell-cycle arrest in the G1, S and G2/M phases, activation of DNA repair, and apoptotic cell death. (Bartek, Jiri, et al., "CHK2 Kinase—A Busy Messenger." *Nature Reviews Molecular Cell Biology.* Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs. Normal cells would still activate other checkpoints and recover, while cancer cells deprived of checkpoints would be more likely to die. It has been demonstrated that a peptide-based inhibitor of CHK2 abrogated the G2 checkpoint and sensitized p53-defective cancer cells to DNA damaging agents. (Pommier, Yves, et al., "Targeting Chk2 Kinase: Molecular Interaction Maps and Therapeutic Rationale." *Current Pharmaceutical Design.* Vol. 11, No. 22 (2005) 2855-2872).

CHK1 inhibitors are known, see for example, International Publication WO 2009/004329, International Publication WO 2008/012635, International Publication WO 2007/090493, International Publication WO 2007/090494, International Publication WO 2006/106326, International Publication WO 2006/120573, International Publication WO 2005/103036, International Publication WO 2005/066163 and International Publication WO 03/028724.

CHK1 inhibitors include SCH900776, PF-00477736, AZD7762, XL844 (see 2008 EORTC Poster #395 [http://www.exelixis.com/eortc/posters/EORTC08_395_XL844-002.pdf]), IC-83, and CHIR-124 (see Tse, Archie N., et al. "CHIR-124, a Novel Potent Inhibitor of Chk1, Potentiates the Cytotoxicity of Topoisomerase I Poisons In vitro and In vivo." *Clin. Cancer Res.* 13(2) (2007) pp. 591-602).

U.S. Provisional Patent Application 61/052,926 describes compounds including (R)—N-(4-(3-aminopiperidin-1-yl)-5-bromo-1H-pyrrolo[2,3-b]pyridin-3-yl)nicotinamide (hereinafter "Compound 1") and (R)—N-(4-(3-aminopiperidin-1-yl)-5-bromo-1H-pyrrolo[2,3-b]pyridin-3-yl)isobutyramide (hereinafter "Compound 2"), (R)—N-(5-bromo-4-(3-(methylamino)piperidin-1-yl)-1H-pyrrolo[2,3-b]pyridin-3-yl)nicotinamide (hereinafter "Compound 3"), (R)—N-(4-(3-aminopiperidin-1-yl)-5-bromo-1H-pyrrolo[2,3-b]pyridin-3-yl)-5-methylnicotinamide (hereinafter "Compound 4"), (R)—N-(4-(3-aminopiperidin-1-yl)-5-bromo-1H-pyrrolo[2,3-b]pyridin-3-yl)cyclopropanecarboxamide (hereinafter "Compound 5"), (R)—N-(4—(3-aminopiperidin-1-yl)-5-bromo-1H-pyrrolo[2,3-b]pyridin-3-yl)-3-methylbutanamide (hereinafter "Compound 6"), and (R)—N-(4-(3-aminopiperidin-1-yl)-5-bromo-1H-pyrrolo[2,3-b]pyridin-3-yl)-2-cyclopropylacetamide (hereinafter "Compound 7"). Compounds 1, 2, 3, 4, 5, 6 and 7 (collectively the "926 CHK1 Inhibitors") are CHK1 inhibitors.

CHK1 inhibitors have been tested as therapeutics for the treatment of diseases. Various dosing schedules have been used in these tests of inhibitors of mitosis. There remains a need for dosing regimens for CHK1 inhibitors that allows potent biological activity with manageable toxicity. There remains a particular need for dosing regimens for CHK1 inhibitors that allows for potentiation of DNA damaging agents dosed in the same regimen.

SUMMARY OF THE INVENTION

Surprisingly, it has been found that administering two or three doses of a CHK1 inhibitor 24 hours after administering a DNA damaging agent may be used to treat cancer.

In one aspect, the present invention relates to a method for treating cancer using CHK1 inhibitors on a dosing regimen.

Another aspect of the present invention provides a method for treating cancer by administering a DNA damaging agent and two doses of a CHK1 inhibitor, wherein the first dose of the CHK1 inhibitor is administered one day after the DNA damaging agent, and the second dose of the CHK1 inhibitor is administered two days after the DNA damaging agent.

Another aspect of the present invention provides a method for treating cancer by administering a DNA damaging agent and three doses of a CHK1 inhibitor, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

Another aspect of the present invention provides a method for treating cancer by administering a DNA damaging agent followed by two doses of a CHK1 inhibitor, wherein the CHK1 inhibitor is administered between the biologically effective dose and the maximum tolerated dose, wherein the first dose of the CHK1 inhibitor is administered one day after the DNA damaging agent, and the second dose of the CHK1 inhibitor is administered two days after the DNA damaging agent.

Another aspect of the present invention provides a method for treating cancer by administering a DNA damaging agent followed by three doses of a CHK1 inhibitor, wherein the CHK1 inhibitor is administered between the biologically effective dose and the maximum tolerated dose, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

Another aspect of the present invention provides a method for treating cancer by administering a DNA damaging agent followed by two doses of an oral CHK1 inhibitor, wherein the first dose of the CHK1 inhibitor is administered one day after the DNA damaging agent, and the second dose of the CHK1 inhibitor is administered two days after the DNA damaging agent.

Another aspect of the present invention provides a method for treating cancer by administering a DNA damaging agent followed by three doses of an oral CHK1 inhibitor, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

Another aspect of the present invention provides a method for treating cancer by administering a DNA damaging agent followed by two doses of an oral CHK1 inhibitor, wherein the CHK1 inhibitor is administered between the biologically effective dose and the maximum tolerated dose, wherein the first dose of the CHK1 inhibitor is administered one day after the DNA damaging agent, and the second dose of the CHK1 inhibitor is administered two days after the DNA damaging agent.

Another aspect of the present invention provides a method for treating cancer by administering a DNA damaging agent followed by three doses of an oral CHK1 inhibitor, wherein the CHK1 inhibitor is administered between the biologically effective dose and the maximum tolerated dose, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

DETAILED DESCRIPTION OF THE INVENTION

Figure 1:
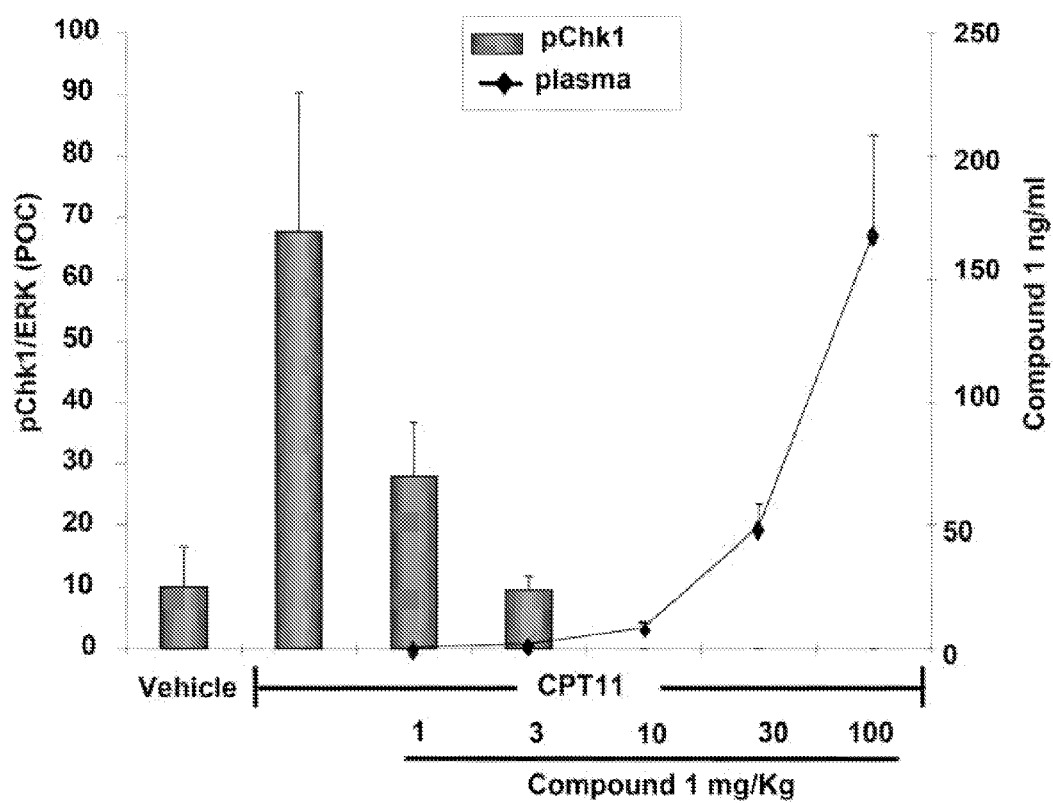
FIG. 1 shows the inhibition of DNA damaging agent induced phosphorylation of CHK1.

Reference will now be made in detail to certain embodiments of the invention. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer including melanoma, and head and neck cancer.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrase "pharmaceutically acceptable" indicates that the substance or composition is compatible chemically and/or toxicologically, with the other ingredients comprising a formulation, and/or the mammal being treated therewith.

Methods of Treating

The present invention provides a method for treating cancer by administering a DNA damaging agent followed by two doses of a CHK1 inhibitor, wherein the first dose of the CHK1 inhibitor is administered one day after the DNA damaging agent, and the second dose of the CHK1 inhibitor is administered two days after the DNA damaging agent.

The present invention also provides a method for treating cancer by administering a DNA damaging agent followed by three doses of a CHK1 inhibitor, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

Exploitation of cell cycle control is a fundamental feature that tumor cells rely on for growth. One mechanism by which this can be accomplished is manipulation of cell cycle checkpoints and DNA damage repair. Evidence suggests that tumor cells can evolve to become refractory to chemotherapy by hyper-activation of DNA-damage repair at the G2/M checkpoint, a cellular process that is dependent upon CHK1. Inhibition of CHK1 removes this route of survival. Administering a CHK1 inhibitor in a regimen with a DNA damaging agent may be more effective than administering the DNA damaging agent alone. It has been found that CHK1 levels are elevated for a prolonged period of time after administration of a DNA damaging agent (See FIGS. 3 and 4). It has also been found that the CHK1 inhibitor should be administered after a 24 hour delay after the administration of the DNA damaging agent (See FIG. 5). Therefore, an appropriate dosing schedule of a CHK1 inhibitor should be delayed 24 hours from the DNA damaging agent, and also be administered long enough to keep CHK1 levels down to enable fewer cells to go through DNA repair.

DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin® (carboplatin), camptothecin, ara-C (cytarabine), 5-FU (fluorouracil), Cytoxan® (cyclophosphamide), Etopophos® or Vepesid® (etoposide phosphate), Vumon® (teniposide), Adriamycin PFS® or Adriamycin RDF® (doxorubicin), daunorubicin, Alimta® (pemetrexed), mitomycin C, fludarabine, chlorambucil, melphalan, hydroxyurea, and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose.

DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin® (carboplatin), camptothecin, ara-C (cytarabine), 5-FU (fluorouracil), Cytoxan® (cyclophosphamide), Etopophos® or Vepesid® (etoposide phosphate), Vumon® (teniposide), Adriamycin PFS® or Adriamycin RDF® (doxorubicin), daunorubicin, Alimta® (pemetrexed), and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose.

In certain embodiments of the present invention, the CHK1 inhibitor is selected from the group consisting of the '926 CHK1 Inhibitors. In certain embodiments of the present invention, the CHK1 inhibitor is selected from the group consisting of Compound 1, Compound 2, Compound 3, Compound 4, Compound 5, Compound 6 and Compound 7. In certain embodiments of the present invention, the CHK1 inhibitor is Compound 1. In certain embodiments of the present invention, the CHK1 inhibitor is Compound 2. In certain embodiments of the present invention, the CHK1 inhibitor is Compound 3. In certain embodiments of the present invention, the CHK1 inhibitor is Compound 4. In certain embodiments of the present invention, the CHK1 inhibitor is Compound 5. In certain embodiments of the present invention, the CHK1 inhibitor is Compound 6. In certain embodiments of the present invention, the CHK1 inhibitor is Compound 7.

In certain embodiments of the present invention, the CHK1 inhibitor is selected from the group consisting of the '926 CHK1 Inhibitors, SCH90076, PF-00477736, AZD7762, XL844, IC-83, and CHIR-124. In certain embodiments of the present invention, the CHK1 inhibitor is selected from the group consisting of SCH90076, PF-00477736, AZD7762, XL844, IC-83, and CHIR-124.

In certain embodiments of the present invention, the CHK1 inhibitor is selected from the group consisting of the '926 CHK1 Inhibitors, PF-00477736, AZD7762, XL844, IC-83, and CHIR-124. In certain embodiments of the present invention, the CHK1 inhibitor is selected from the group consisting of PF-00477736, AZD7762, XL844, IC-83, and CHIR-124.

In certain embodiments of the present invention, the CHK1 inhibitor does not include the '926 CHK1 Inhibitors.

In certain embodiments, the invention provides a method for treating cancer. More particularly, cancers that may be treated by the compositions and methods of the invention include, but are not limited to: Soft Tissue Cancers: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood and bone marrow (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. The term "cancerous cell" as provided herein, includes a cell afflicted by any one of the above identified conditions.

In certain embodiments of the present invention, the cancer is selected from colorectal cancer (including Ras mutations), small cell lung cancer, non-small cell lung cancer (including Ras mutations), glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer.

In certain embodiments of the present invention, the cancer is selected from colorectal cancer (including Ras mutations), small cell lung cancer, non-small cell lung cancer, glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer.

In certain embodiments of the present invention, the cancer is a solid tumor cancer.

In certain embodiments of the present invention, the cancer is selected from pancreatic cancer, ovarian cancer and colorectal cancer.

In certain embodiments of the present invention, the cancer is selected from colorectal cancer (including Ras mutations), small cell lung cancer, non-small cell lung cancer, and glioma. In a further embodiment, the DNA damaging agent is irinotecan.

In certain embodiments of the present invention, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer. In a further embodiment, the DNA damaging agent is gemcitabine.

In certain embodiments of the present invention, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma. In a further embodiment, the DNA damaging agent is selected from the group consisting of cisplatin, oxaliplatin, and carboplatin.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer. In a further embodiment, the DNA damaging agent is cytarabine.

The administration of the DNA damaging agent starts the timing of the dosing regimen. This first dose (of the DNA damaging agent) is said to be on day one. The present invention provides two or three doses of a CHK1 inhibitor, wherein the first dose is on day two, the second dose is on day three, and the third dose is on day four. The administration of the CHK1 inhibitor should follow the administration of the DNA damaging agent by at least one day, or approximately 24 hours. However, the first dose of CHK1 inhibitor administered need not be exactly 24 hours after the administration of the DNA damaging agent. This is just a convenient way of saying the CHK1 inhibitor should be dosed the day after the DNA damaging agent. Therefore, administration of the CHK1 inhibitor one day after the DNA damaging agent includes administering the CHK1 inhibitor 18 to 36 hours after the DNA damaging agent. Furthermore, administration of the CHK1 inhibitor two days after the DNA damaging agent includes administering the CHK1 inhibitor 36 to 60 hours after the DNA damaging agent. Finally, administration of the CHK1 inhibitor three days after the DNA damaging agent includes administering the CHK1 inhibitor 60 to 90 hours after the DNA damaging agent.

Alternatively, it can be said, the first dose of the CHK1 inhibitor is administered within 18 to 30 hours after the administration of the DNA damaging agent, the second dose of the CHK1 inhibitor is administered within 30 to 50 hours after the administration of the DNA damaging agent, and the third dose of the CHK1 inhibitor is administered within 50 to 90 hours after the administration of the DNA damaging agent.

The present invention provides a method for treating cancer by administering a DNA damaging agent followed by two or three doses of a CHK1 inhibitor, wherein the first dose of the CHK1 inhibitor is administered one day after the DNA damaging agent, and the second dose of the CHK1 inhibitor is administered two days after the DNA damaging agent, and optionally a third dose is administered three days after the DNA damaging agent.

One embodiment of the present invention provides a method for treating cancer by administering a DNA damaging agent followed by two doses of a CHK1 inhibitor, wherein the CHK1 inhibitor is administered between the biologically effective dose and the maximum tolerated dose, wherein the first dose of the CHK1 inhibitor is administered one day after the DNA damaging agent, and the second dose of the CHK1 inhibitor is administered two days after the DNA damaging agent.

Another embodiment of the present invention provides a method for treating cancer by administering a DNA damaging agent followed by three doses of a CHK1 inhibitor, wherein the CHK1 inhibitor is administered between the biologically effective dose and the maximum tolerated dose, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

The CHK1 inhibitor must be dosed at least at a level to reach the desired biological effect. Thus, an effective dosing regimen will dose at least a minimum amount that reaches the desired biological effect, or biologically effective dose.

In one embodiment of the present invention, the desired biological effect of a CHK1 inhibitor is an 80% or greater inhibition in pCHK1 following administration of a DNA damaging agent (relative to the administration of the DNA damaging agent alone).

In another embodiment of the present invention, the desired biological effect of a CHK1 inhibitor is a 90% or greater inhibition in pCHK1 following administration of a DNA damaging agent (relative to the administration of the DNA damaging agent alone).

In another embodiment of the present invention, the desired biological effect of a CHK1 inhibitor is a 95% or greater inhibition in pCHK1 following administration of a DNA damaging agent (relative to the administration of the DNA damaging agent alone).

In another embodiment of the present invention, the desired biological effect of a CHK1 inhibitor is a 66% or greater inhibition in p-cdc2 following administration of a DNA damaging agent (relative to the administration of the DNA damaging agent alone).

However, the dose should not be so high as to outweigh the benefit of the biological effect with unacceptable side effects. Therefore, an effective dosing regimen will dose no more than the maximum tolerated dose ("MTD"). The present invention provides a method of treating a patient with a dosing regimen that includes two or three doses of a CHK1 inhibitor, wherein the doses of the CHK1 inhibitor are between the biologically effective dose and the maximum tolerated dose.

The maximum tolerated dose is defined as the highest dose that produces an acceptable incidence of dose-limiting toxicities ("DLT"). Doses that cause an unacceptable rate of DLT are considered non-tolerated. Typically, the MTD for a particular schedule is established in phase 1 clinical trials. These are usually conducted in patients by starting at a safe starting dose of 1/10 the severe toxic dose ("STD10") in rodents (on a mg/m² basis) and accruing patients in cohorts of three, escalating the dose according to a modified Fibonacci sequence in which ever higher escalation steps have ever decreasing relative increments (e.g., dose increases of 100%, 65%, 50%, 40%, and 30% to 35% thereafter). The dose escalation is continued in cohorts of three patients until a non-tolerated dose is reached. The next lower dose level that produces an acceptable rate of DLT is considered to be the MTD.

Also, the MTD of a CHK1 inhibitor varies depending on the specific inhibitor, species and dosing schedule. For instance, dosing only on day one versus days one and two versus days one through three over a seven, fourteen, twenty-one or twenty-eight day dosing cycle may all have different MTDs. However, as discussed above, an effective dosing schedule needs to dose the inhibitor high enough to be biologically effective. Dosing on day one only may reach the biologically effective dose, but may not be long enough to keep damaged cells from DNA repair. Alternatively, dosing days one through three may dose long enough, but may not dose high enough to reach the biologically effective dose. This may be due to the MTD of dosing for three days being lower than the biologically effective dose. Thus, an effective dosing schedule will have an MTD equal to or greater than the biologically effective dose.

In one embodiment of the present invention, the two or three doses of the CHK1 inhibitor are administered between the biologically effective dose and the maximum tolerated dose.

In another embodiment of the present invention, the two or three doses of the CHK1 inhibitor are administered at the maximum tolerated dose.

Typically when treating cancer, patients are dosed at the MTD of a particular compound so that the maximum benefit in the treatment can be reached. Accordingly, one embodiment of the present invention provides a method of treating cancer by administering two or three doses of a CHK1 inhibitor, wherein the doses of the CHK1 inhibitor are at the maximum tolerated dose of the inhibitor.

One embodiment of the present invention provides a method for treating cancer by administering a DNA damaging agent followed by two doses of an oral CHK1 inhibitor, wherein the first dose of the CHK1 inhibitor is administered one day after the DNA damaging agent, and the second dose of the CHK1 inhibitor is administered two days after the DNA damaging agent.

Another embodiment of the present invention provides a method for treating cancer by administering a DNA damaging agent followed by three doses of an oral CHK1 inhibitor, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

An oral CHK1 inhibitor is a CHK1 inhibitor that may be administered orally. When the CHK1 inhibitor is administered orally, it may be formulated as a pill, hard or soft capsule, tablet, lozenge, aqueous or oily suspension, emulsion, dispersible powders or granules, syrup, elixir, etc., with a pharmaceutically acceptable carrier or excipient.

The '926 CHK1 Inhibitors are oral CHK1 inhibitors.

One embodiment of the present invention provides a method for treating cancer by administering a DNA damaging agent followed by two doses of an oral CHK1 inhibitor, wherein the CHK1 inhibitor is administered between the biologically effective dose and the maximum tolerated dose, wherein the first dose of the CHK1 inhibitor is administered one day after the DNA damaging agent, and the second dose of the CHK1 inhibitor is administered two days after the DNA damaging agent.

Another embodiment of the present invention provides a method for treating cancer by administering a DNA damaging agent followed by three doses of an oral CHK1 inhibitor, wherein the CHK1 inhibitor is administered between the biologically effective dose and the maximum tolerated dose, wherein the first dose of the CHK1 inhibitor is administered one day after the DNA damaging agent, the second dose of the CHK1 inhibitor is administered two days after the DNA damaging agent, and the third dose of the CHK1 inhibitor is administered three days after the DNA damaging agent.

In certain embodiments of the present invention, the dose of the CHK1 inhibitor may be broken into two daily administrations (i.e., BID dosing). In this embodiment, the first dose of the CHK1 inhibitor includes two administrations one day after the administration of the DNA damaging agent. The two administrations are generally spaced out over the day. This will also include two administrations on day two, and optionally on day three.

One embodiment of the present invention provides a method for treating cancer by administering a DNA damaging agent followed by four doses of a CHK1 inhibitor, wherein the first two doses of the CHK1 inhibitor are administered one day after the DNA damaging agent, and the third and fourth doses of the CHK1 inhibitor are administered two days after the DNA damaging agent.

Another embodiment of the present invention provides a method for treating cancer by administering a DNA damaging agent followed by six doses of a CHK1 inhibitor, wherein the first two doses of the CHK1 inhibitor are administered one day after the DNA damaging agent, the third and fourth doses of the CHK1 inhibitor are administered two days after the DNA damaging agent, and the fifth and sixth dose of the CHK1 inhibitor are administered three days after the DNA damaging agent.

One embodiment of the present invention provides a method for treating cancer by administering a DNA damaging agent followed by four doses of a CHK1 inhibitor, wherein the CHK1 inhibitor is administered between the biologically effective dose and the maximum tolerated dose, wherein the first two doses of the CHK1 inhibitor are administered one day after the DNA damaging agent, and the third and fourth doses of the CHK1 inhibitor are administered two days after the DNA damaging agent.

Another embodiment of the present invention provides a method for treating cancer by administering a DNA damaging agent followed by six doses of a CHK1 inhibitor, wherein the CHK1 inhibitor is administered between the biologically effective dose and the maximum tolerated dose, wherein the first two doses of the CHK1 inhibitor are administered one day after the DNA damaging agent, the third and fourth doses of the CHK1 inhibitor are administered two days after the DNA damaging agent, and the fifth and sixth dose of the CHK1 inhibitor are administered three days after the DNA damaging agent.

One embodiment of the present invention provides a method for treating cancer by administering a DNA damaging agent followed by four doses of an oral CHK1 inhibitor, wherein the first two doses of the CHK1 inhibitor are administered one day after the DNA damaging agent, and the third and fourth doses of the CHK1 inhibitor are administered two days after the DNA damaging agent.

Another embodiment of the present invention provides a method for treating cancer by administering a DNA damaging agent followed by six doses of an oral CHK1 inhibitor, wherein the first two doses of the CHK1 inhibitor are administered one day after the DNA damaging agent, the third and fourth doses of the CHK1 inhibitor are administered two days after the DNA damaging agent, and the fifth and sixth dose of the CHK1 inhibitor are administered three days after the DNA damaging agent.

One embodiment of the present invention provides a method for treating cancer by administering a DNA damaging agent followed by four doses of an oral CHK1 inhibitor, wherein the CHK1 inhibitor is administered between the biologically effective dose and the maximum tolerated dose, wherein the first two doses of the CHK1 inhibitor are administered one day after the DNA damaging agent, and the third and fourth doses of the CHK1 inhibitor are administered two days after the DNA damaging agent.

Another embodiment of the present invention provides a method for treating cancer by administering a DNA damaging agent followed by six doses of an oral CHK1 inhibitor, wherein the CHK1 inhibitor is administered between the biologically effective dose and the maximum tolerated dose, wherein the first two doses of the CHK1 inhibitor are administered one day after the DNA damaging agent, the third and fourth doses of the CHK1 inhibitor are administered two days after the DNA damaging agent, and the fifth and sixth dose of the CHK1 inhibitor are administered three days after the DNA damaging agent.

Another embodiment of the present invention provides a method for treating a patient afflicted with cancer comprising administering a DNA damaging agent and two doses of a '926 CHK1 inhibitor, wherein the first dose of the '926 CHK1 inhibitor is administered one day after the DNA damaging agent, and the second dose of the '926 CHK1 inhibitor is administered two days after the DNA damaging agent.

Another embodiment of the present invention provides a method for treating a patient afflicted with cancer comprising administering a DNA damaging agent and three doses of a '926 CHK1 inhibitor, wherein the first dose of the '926 CHK1 inhibitor is administered one day after the DNA damaging agent, the second dose of the '926 CHK1 inhibitor is administered two days after the DNA damaging agent, and the third dose of the '926 CHK1 inhibitor is administered three days after the DNA damaging agent.

Another embodiment of the present invention provides a method for treating a patient afflicted with cancer comprising administering a DNA damaging agent and four doses of a '926 CHK1 inhibitor, wherein the first and second doses of the '926 CHK1 inhibitor are administered one day after the DNA damaging agent, and the third and fourth doses of the '926 CHK1 inhibitor are administered two days after the DNA damaging agent.

Another embodiment of the present invention provides a method for treating a patient afflicted with cancer comprising administering a DNA damaging agent and six doses of a '926 CHK1 inhibitor, wherein the first and second doses of the '926 CHK1 inhibitor are administered one day after the DNA damaging agent, the third and fourth doses of the '926 CHK1 inhibitor are administered two days after the DNA damaging agent, and the fifth and sixth doses of the '926 CHK1 inhibitor are administered three days after the DNA damaging agent.

Another embodiment of the present invention provides the use of a '926 CHK1 inhibitor for the preparation of a pharmaceutical composition for the treatment of cancer comprising administering two doses of the '926 CHK1 inhibitor composition following the administration of a DNA damaging agent, wherein the first dose of the '926 CHK1 inhibitor is administered one day after the DNA damaging agent, and the second dose of the '926 CHK1 inhibitor is administered two days after the DNA damaging agent.

Another embodiment of the present invention provides the use of a '926 CHK1 inhibitor for the preparation of a pharmaceutical composition for the treatment of cancer comprising administering three doses of the '926 CHK1 inhibitor composition following the administration of a DNA damaging agent, wherein the first dose of the '926 CHK1 inhibitor is administered one day after the DNA damaging agent, the second dose of the '926 CHK1 inhibitor is administered two days after the DNA damaging agent, and the third dose of the '926 CHK1 inhibitor is administered three days after the DNA damaging agent.

Another embodiment of the present invention provides the use of a '926 CHK1 inhibitor for the preparation of a pharmaceutical composition for the treatment of cancer comprising administering four doses of the '926 CHK1 inhibitor composition following the administration of a DNA damaging agent, wherein the first and second doses of the '926 CHK1 inhibitor are administered one day after the DNA damaging agent, and the third and fourth doses of the '926 CHK1 inhibitor are administered two days after the DNA damaging agent.

Another embodiment of the present invention provides the use of a '926 CHK1 inhibitor for the preparation of a pharmaceutical composition for the treatment of cancer comprising administering six doses of the '926 CHK1 inhibitor composition following the administration of a DNA damaging agent, wherein the first and second doses of the '926 CHK1 inhibitor are administered one day after the DNA damaging agent, the third and fourth doses of the '926 CHK1 inhibitor are administered two days after the DNA damaging agent, and the fifth and sixth doses of the '926 CHK1 inhibitor are administered three days after the DNA damaging agent.

EXAMPLES

In order to illustrate the invention, the following Examples are included. However, it is to be understood that these Examples do not limit the invention and are only meant to suggest a method of practicing the invention.

Example 1

Chk1 Inhibitors have Potent Pharmacodynamic Activity

Female nude mice were inoculated subcutaneously with $5 \times 10^6$ HT-29 tumor cells in 1×PBS (100 µL). Eleven days later, the mice were randomized into groups of 3 with an average tumor volume in each group of approximately 300 mm$^3$. Sorted animals were administered CPT11 (100 mg/kg; IP) for 24 hours, and then challenged with Compound 1 or Compound 2.

Compound 1 (1 mg/Kg, 3 mg/Kg, 10 mg/Kg, 30 mg/Kg, and 100 mg/Kg; PO) was administered and tumors were harvested 2 hours post dose. Phosphorylation of CHK1 (s296) was assessed by immunoblot and normalized to total ERK expression. Results were expressed as percent of control ("POC"). Results are shown in FIG. 1.

Figure 2:
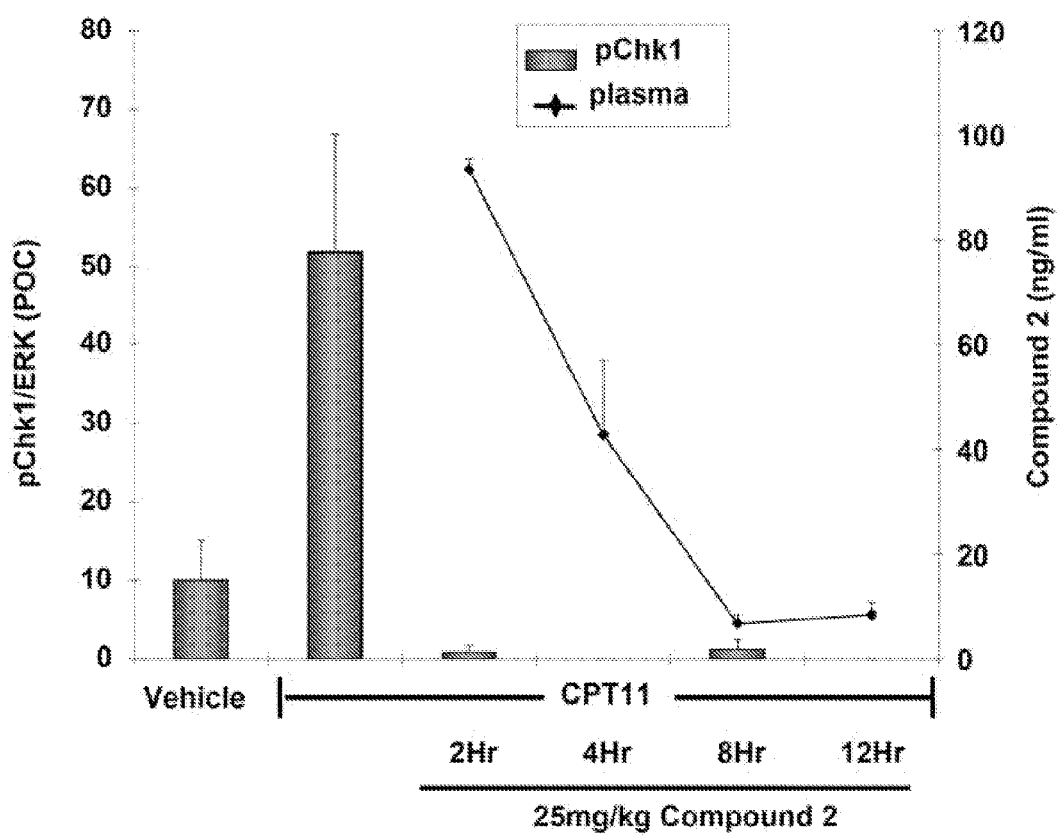
FIG. 2 shows the inhibition of DNA damaging agent induced phosphorylation of CHK1.

Compound 2 (25 mg/kg; PO) was administered and tumors were harvested 2 hours, 4 hours, 8 hours and 12 hours post dose. Phosphorylation of CHK1 (s296) was assessed by immunoblot and normalized to total ERK expression. Results were expressed as POC. Results are shown in FIG. 2.

Example 2

Replication Inhibitors Induce Long Term Activation of Chk1 In Vivo

Figure 3:
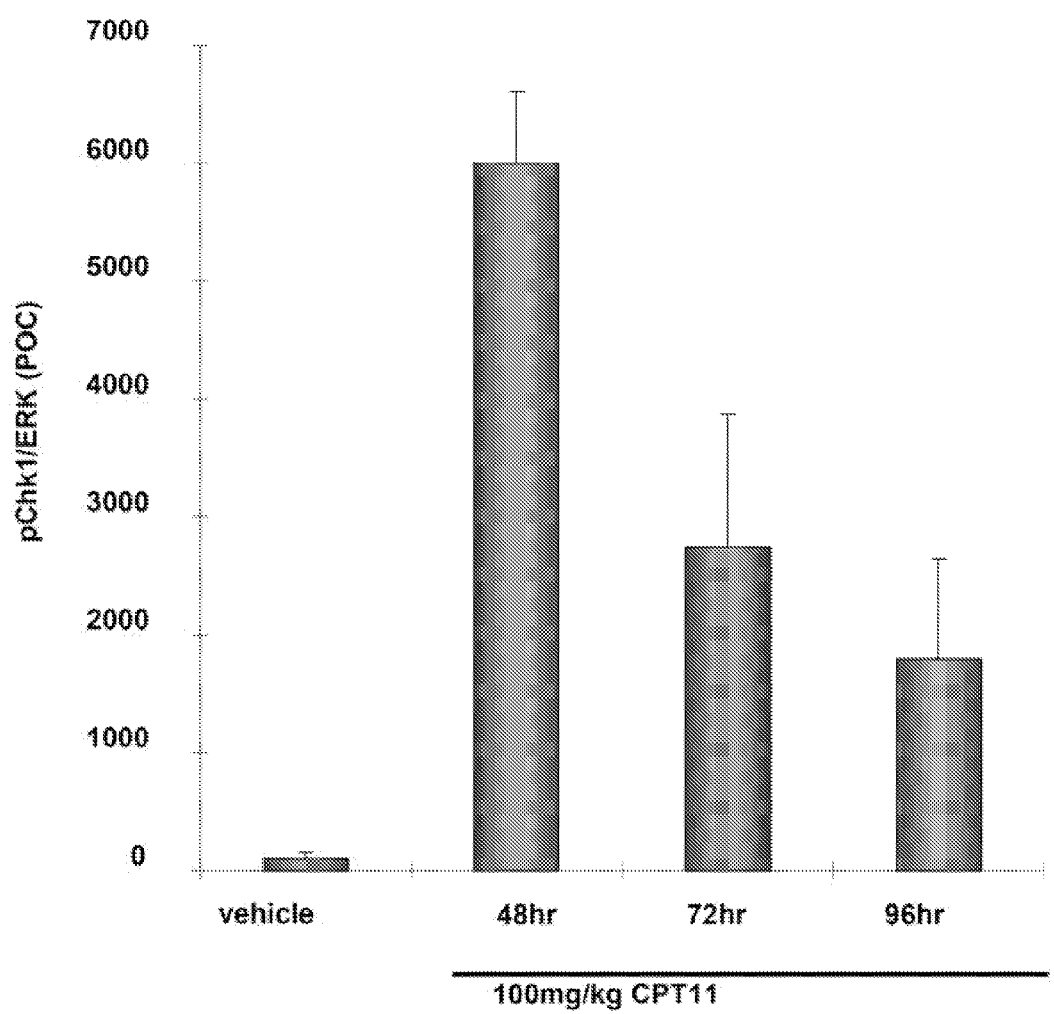
FIG. 3 shows the phosphorylation of CHK1 post-administration of a DNA damaging agent.
Figure 4:
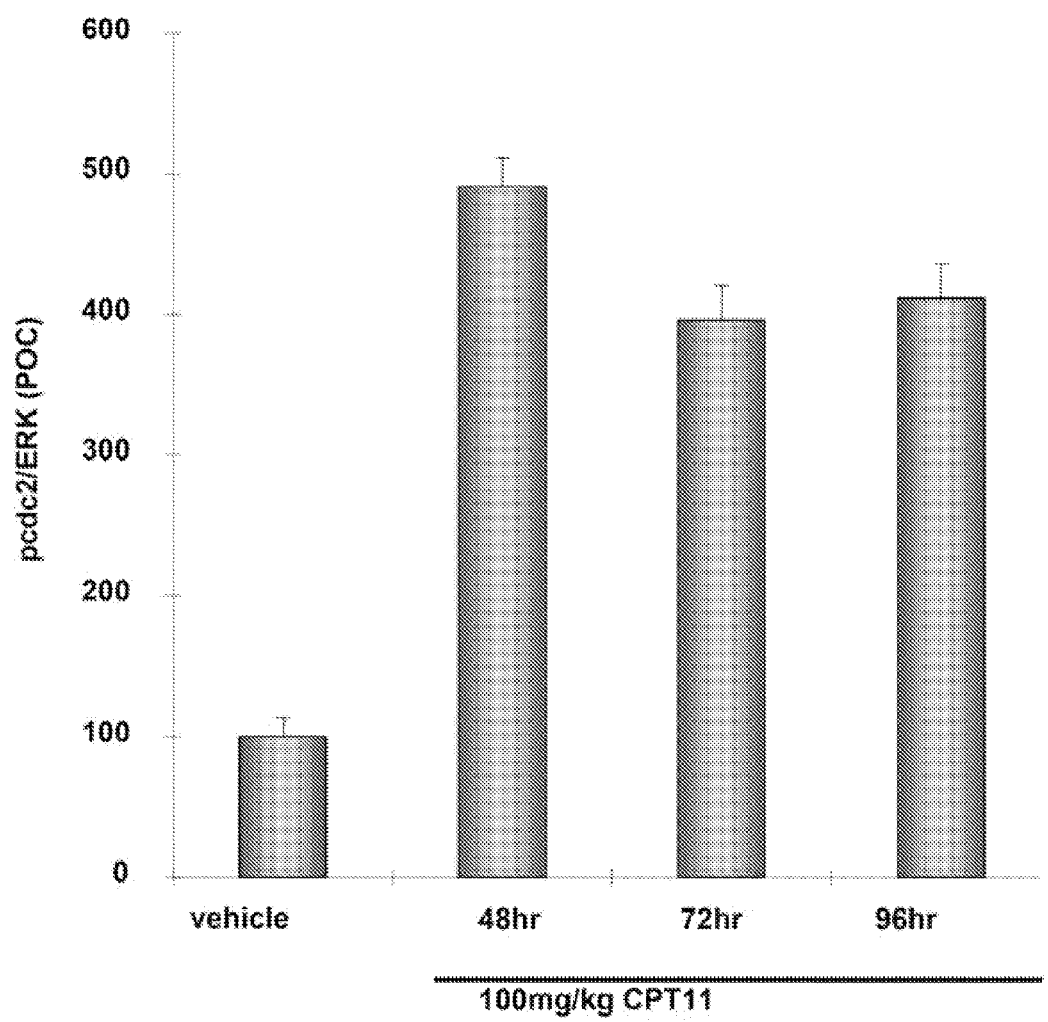
FIG. 4 shows the phosphorylation of cdc2 post-administration of a DNA damaging agent.

Female nude mice were inoculated subcutaneously with $5 \times 10^6$ HT-29 tumor cells in 1×PBS (100 µL). Twenty days later, mice were randomized into groups of 3 with an average tumor volume in each group of approximately 390 mm$^3$. HT-29 tumor bearing female nude mice were administered CPT11 (100 mg/kg; IP), and the tumors were collected for analysis at 48 hours, 72 hours and 96 hours post dose. Phosphorylation of CHK1 and cdc2 were assessed by immunoblot and normalized to total ERK expression. Results were expressed as POC. Results are shown in FIGS. 3 and 4.

Example 3

Figure 5:
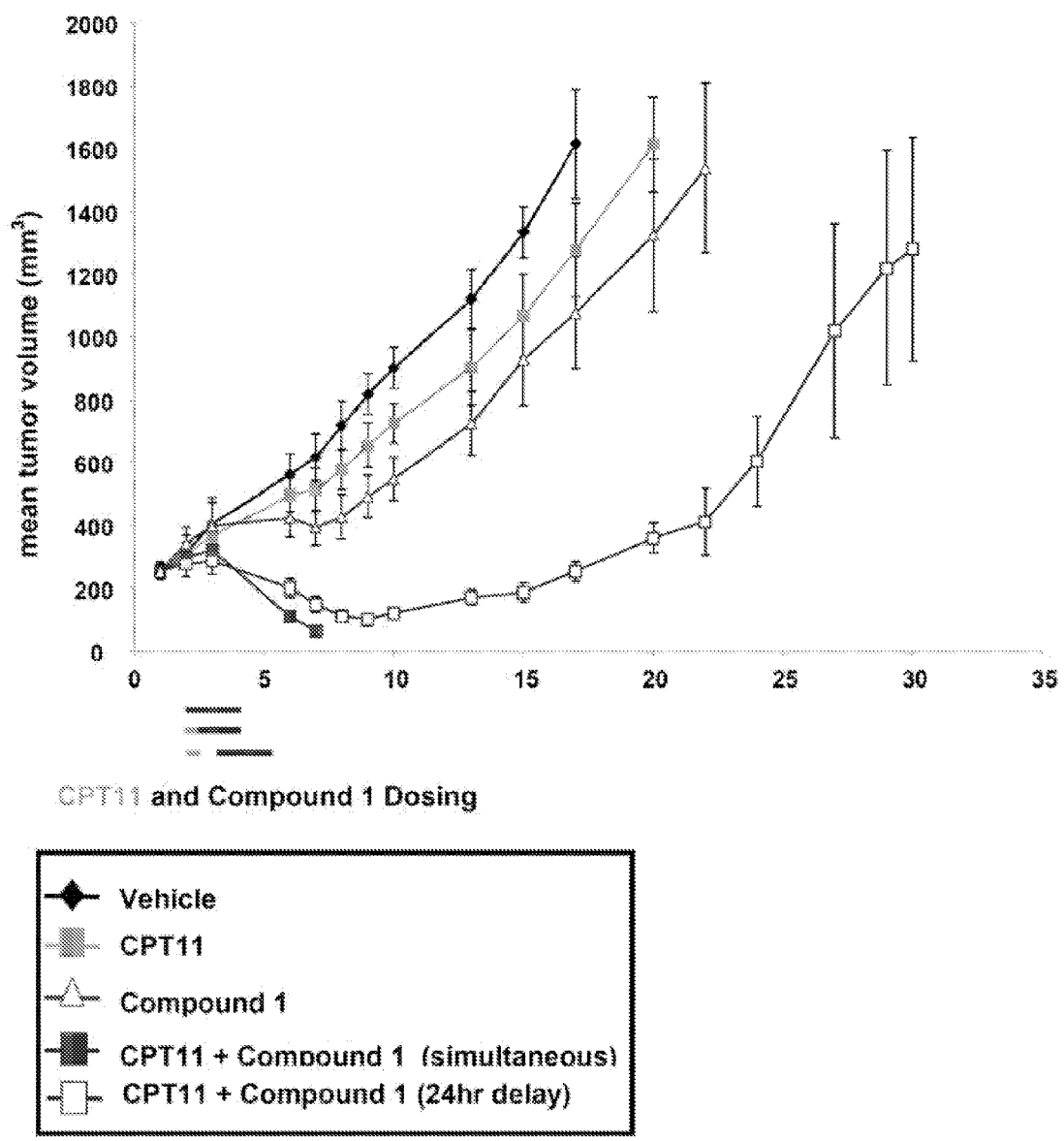
FIG. 5 shows a tumor growth inhibition ("TGI") experiment in nude mice with subcutaneous HT-29 xenografts.

Delayed Administration of Compound 1 Post Chemotherapy Provides Superior Tolerability Female nude mice were inoculated subcutaneously with $5 \times 10^6$ HT-29 tumor cells in 1×PBS (100 µL). Twelve days later, mice were randomized into groups of 6 with an average tumor volume in each group of approximately 250 mm$^3$. Sorted animals were administered a single dose of CPT11 (100 mg/kg; IP) on day 2, followed by Compound 1 (50 mg/kg; PO, BID) either simultaneously or 24 hours post CPT11 administration, for 3 consecutive days. Tumor size and animal body weight were measured over the course of the study on the days indicated with data points in FIG. 5. Tumor volume was calculated using the formula: volume=(width$^2$× length)/2. The results are shown in FIG. 5 and the tolerability results are shown in Table 1:

TABLE 1

| Treatment | Maximum % Body Weight Loss | % Mortality |
| --- | --- | --- |
| Vehicle | 5.5, Day 13 | 0 |
| CPT11 | 3.9, Day 13 | 0 |
| Compound 1 | 3.9, Day 13 | 0 |
| Combo simultaneous | N/A | 100 |
| Combo 24 hour delay | 18.3, Day 9 | 17 |

Example 4

Administration of Compound 2 at Least 24 Hours Post Chemotherapy Provides Optimal Tolerability Naïve female nude mice were administered CPT11 (100 mg/kg; IP) on a Q10D×2 cycles schedule. Compound 2 (25 mg/kg; PO, BID, for 3 days per each CPT11 cycle) administration was initiated 12, 24, or 48 hours post CPT11. Tolerability results are shown in Table 2:

TABLE 2

| Treatment | Maximum % Body Weight Loss | % Mortality |
| --- | --- | --- |
| Vehicle | 0.5, Day 14 | 0 |
| CPT11 | 3.4, Day 14 | 0 |
| Compound 2 | 0.3, Day 17 | 0 |
| CPT11 + Compound 2 (12 hr delay) | 17.1, Day 7 | 12.5 |
| CPT11 + Compound 2 (24 hr delay) | 2.1, Day 14 | 0 |
| CPT11 + Compound 2 (48 hr delay) | 2.6 Day 3 | 0 |

Example 5

Extended CHK1 Inhibition Augments Efficacy

Figure 6:
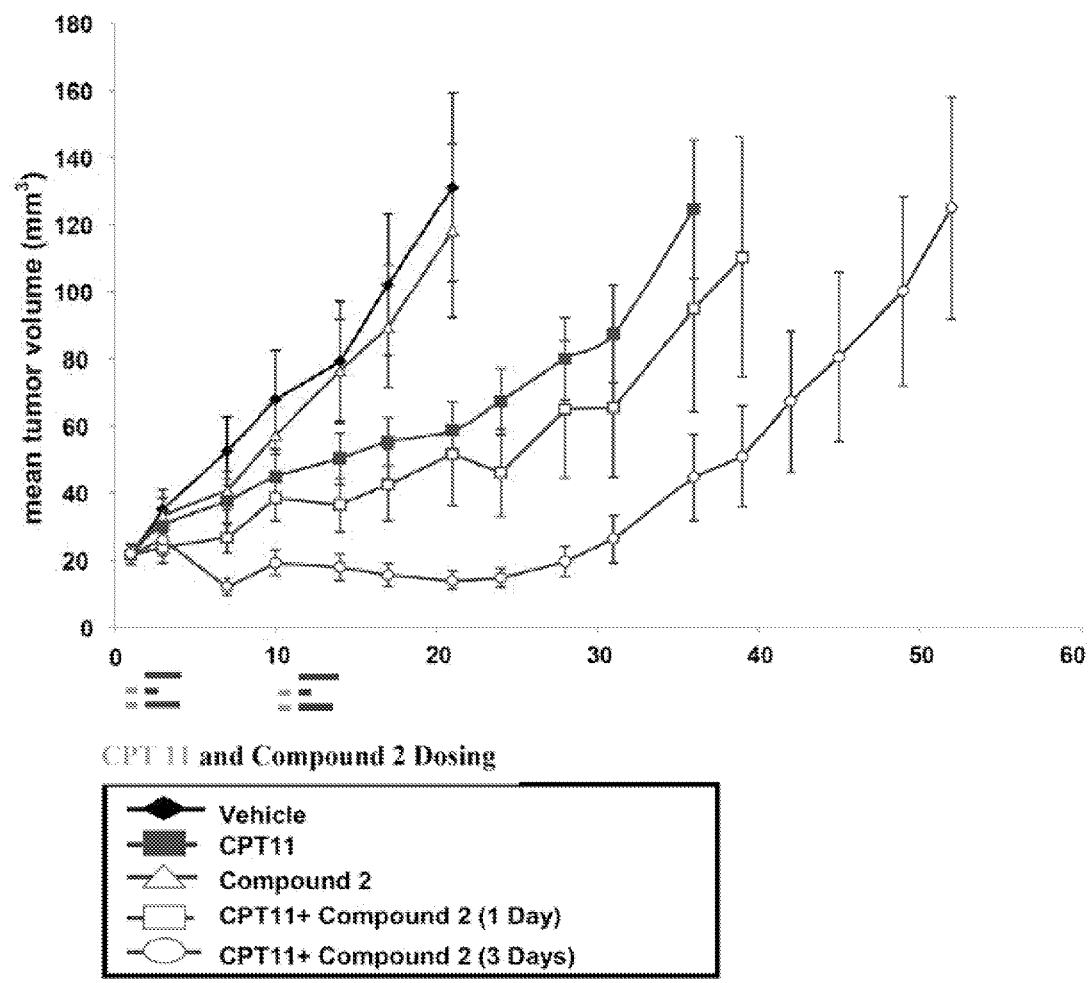
FIG. 6 shows a TGI experiment in nude mice with subcutaneous HT-29 xenografts.

Female nude mice were inoculated subcutaneously with $5 \times 10^6$ HT-29 tumor cells in 1×PBS (100 µL). Twelve days later, mice were randomized into groups of 8 with an average tumor volume in each group of approximately 215 mm³. Sorted animals were administered CPT11 (100 mg/kg; IP) on a Q10D×2 cycles schedule. Compound 2 (25 mg/kg; PO, BID) administration initiated 24 hours post CPT11 for 1 or 3 days as indicated. Tumor size and animal body weight were measured over the course of the study on the days indicated with data points in FIG. 6. Tumor volume was calculated using the formula: volume=(width²×length)/2. No mortalities occurred over the course of this study. Results are shown in FIG. 6 and tolerability results are shown in Table 3:

TABLE 3

| Treatment | Growth Delay (Days) | % Regression | Maximum % Body Weight Loss |
|---|---|---|---|
| Vehicle | N/A | N/A | 1.5, Day 3 |
| Compound 2 | 1.8 | N/A | 7.2, Day 3 |
| CPT11 | 16 | N/A | 1.1, Day 17 |
| Combo 1 day | 20.8 | N/A | 6.1, Day 3 |
| Combo 3 days | 32.4 | 45 | 4.5, Day 3 |

Example 6

Extended Dosing of Compound 1 Induces Superior Inhibition of CPT11 Induced Phospho-cdc2

Figure 7:
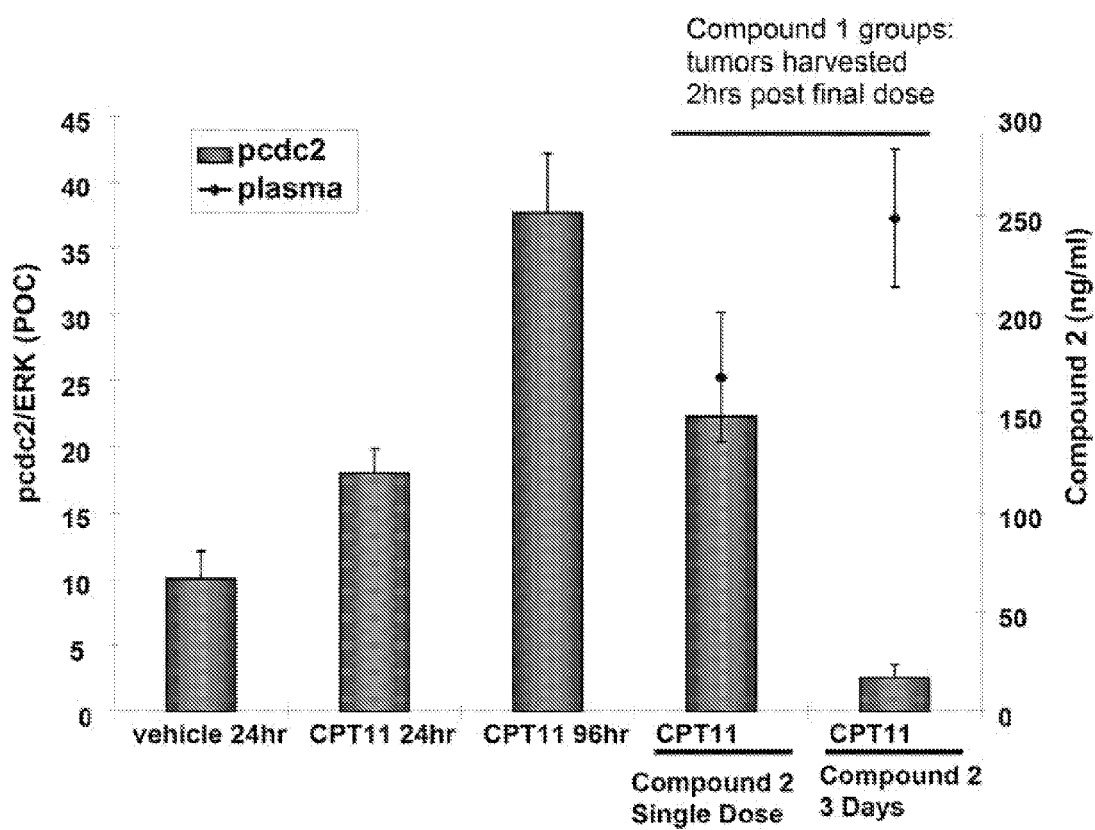
FIG. 7 shows the inhibition of DNA damaging agent induced phosphorylation of cdc2.

Female nude mice were inoculated subcutaneously with 5×10⁶ HT-29 tumor cells in 1×PBS (100 μL). Twenty four days later, mice were randomized into groups of 3 with an average tumor volume in each group of approximately 450 mm³. Sorted animals were administered CPT11 (100 mg/kg; IP) as a single agent, and tumors were harvested at 24 hours and 96 hours post dose. For combination groups, Compound 2 (25 mg/kg; PO) dosing commenced 24 hours after administration of CPT11 (100 mg/kg). Compound 2 was given as a single dose, or alternatively for 3 consecutive days on a BID schedule. All tumors from animals dosed with Compound 2 were harvested 2 hours post dose. Phosphorylation of cdc2 was assessed by immunoblot and normalized to total ERK expression. Results are expressed as POC. Compound 2 exposure following a single dose or administration for 3 days was not statistically different (t-test>0.05). Results are shown in FIG. 7.

Example 7

Extended Dosing of Compound 5 Induces Dose-Related Inhibition of CPT11 Induced Phospho-cdc2

Figure 8:
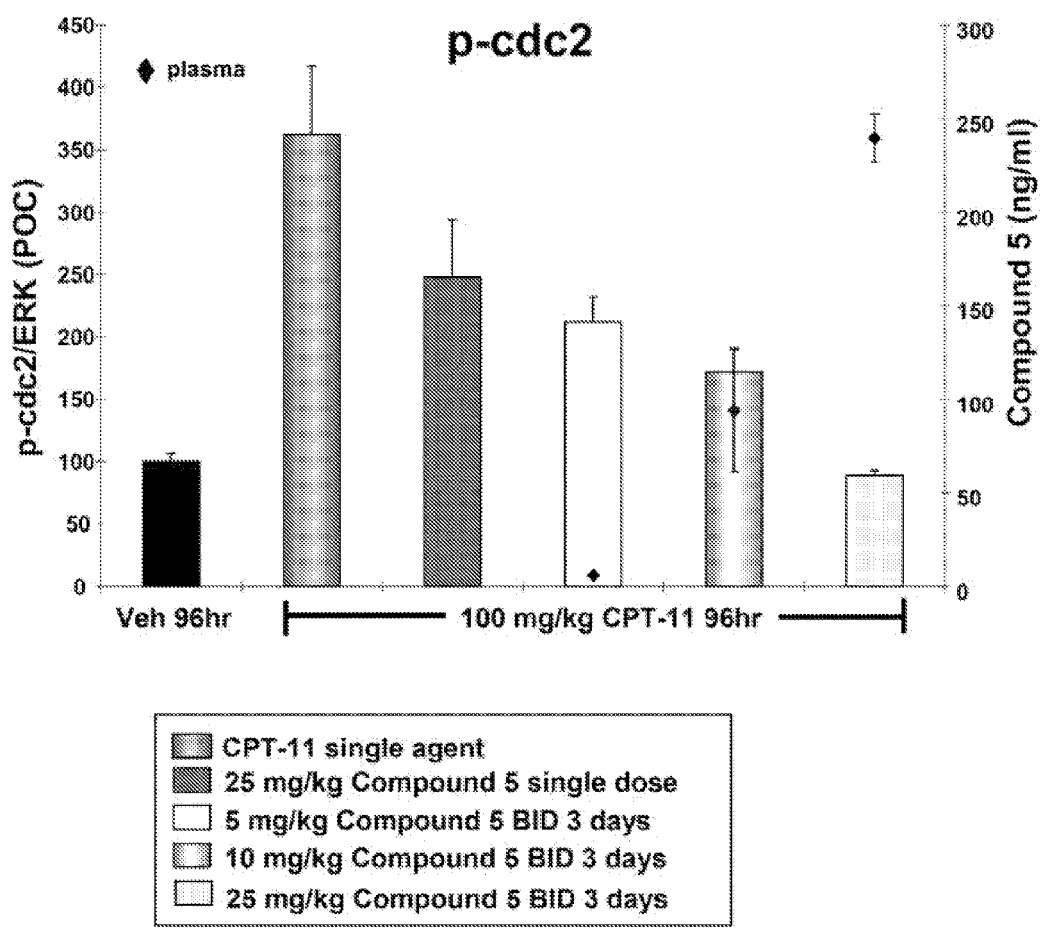
FIG. 8 shows the inhibition of DNA damaging agent induced phosphorylation of cdc2.

Female nude mice were inoculated subcutaneously with 5×10⁶ HT-29 tumor cells in 1×PBS (100 μL). Twenty nine days later, mice were randomized into groups of 3 with an average tumor volume in each group of approximately 500 mm³. Sorted animals were administered CPT11 (100 mg/kg; IP) as a single agent, and tumors were harvested at 96 hours post dose. For combination groups, Compound 5 (5, 10, or 25 mg/kg; PO) dosing commenced 24 hours after administration of CPT11 (100 mg/kg). Compound 5 was given as a single dose at 25 mg/kg, or alternatively 5, 10, or 25 mg/kg doses were given for 3 consecutive days on BID schedules. All tumors from animals dosed with Compound 5 were harvested 96 hours post CPT11 dose. Phosphorylation of cdc2 was assessed by immunoblot and normalized to total ERK expression. Results are expressed as POC. Results are shown in FIG. 8.

Example 8

Figure 9:
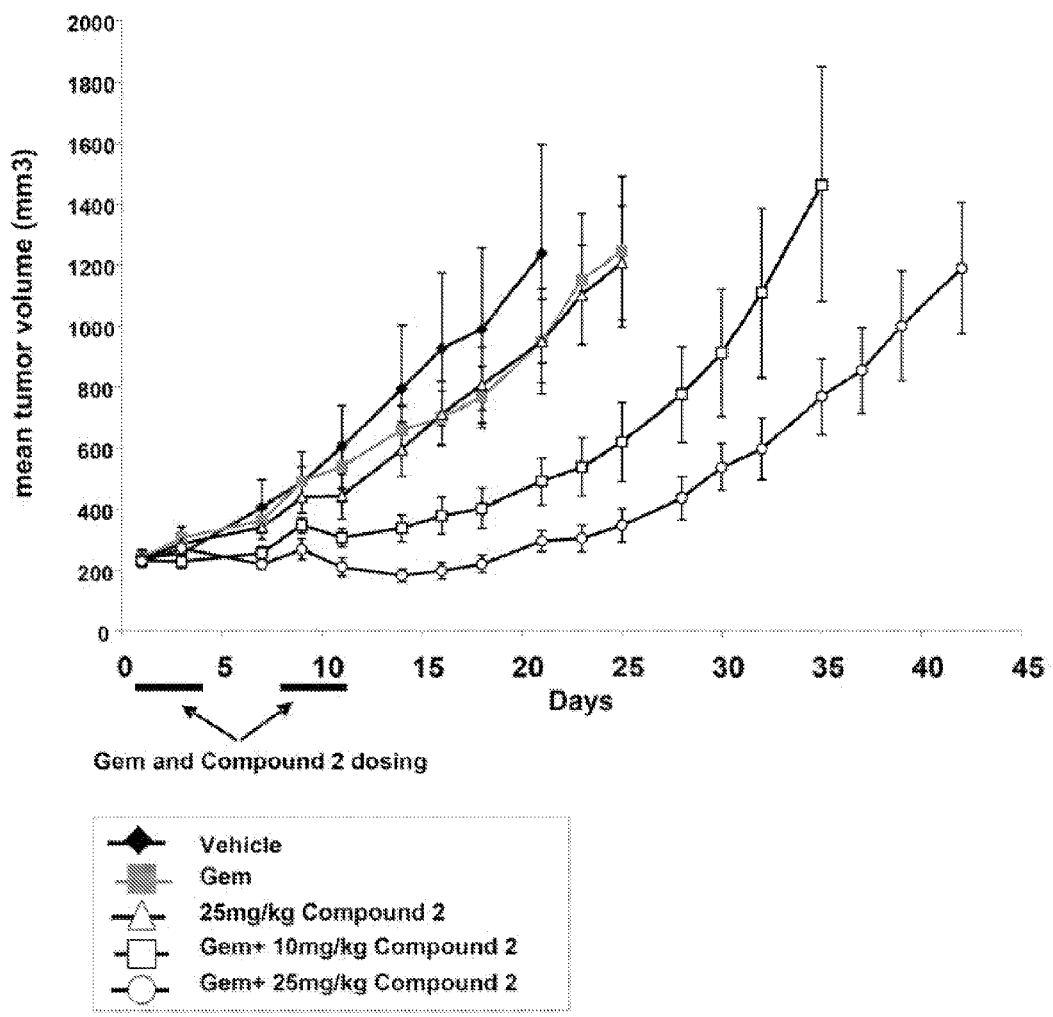
FIG. 9 shows a TGI experiment in nude mice with subcutaneous HT-29 xenografts.

Compound 2 Shows Dose Related Inhibition of Tumor Growth in Combination with Gemcitabine Female nude mice were inoculated subcutaneously with 5×10⁶ HT-29 tumor cells in 1×PBS (100 μL). Fourteen days later, mice were randomized into groups of 8 with an average tumor volume in each group of approximately 260 mm³. Sorted animals were administered gemcitabine (140 mg/kg; IP) on a Q7D×2 cycles schedule. Compound 2 (10 or 25 mg/kg; PO, BID) administration was initiated 24 hours post gemcitabine and endured for 3 days as indicated. Tumor size and animal body weight were measured over the course of the study on the days indicated with data points in FIG. 9. Tumor volume was calculated using the formula: volume=(width²×length)/2. No mortalities occurred over the course of this study. Results are shown in FIG. 9, while tumor growth metrics and tolerability results are shown in the Table 4:

TABLE 4

| Treatment | Growth Delay (Days) | % Regression | Maximum % Body Weight Loss |
|---|---|---|---|
| Vehicle | N/A | N/A | 1.22, Day 7 |
| Gemcitabine | 4.39 | N/A | 3.16, Day 3 |
| Compound 2 | 4.78 | N/A | 0.54, Day 7 |
| Gemcitabine + Compound 2 (10 mg/kg) | 15.97 | 1.44, Day 3 | 7.5, Day 14 |
| Gemcitabine + Compound 2 (25 mg/kg) | 32.77 | 20.43, Day 14 | 8.45, Day 14 |

Example 9

Figure 10:
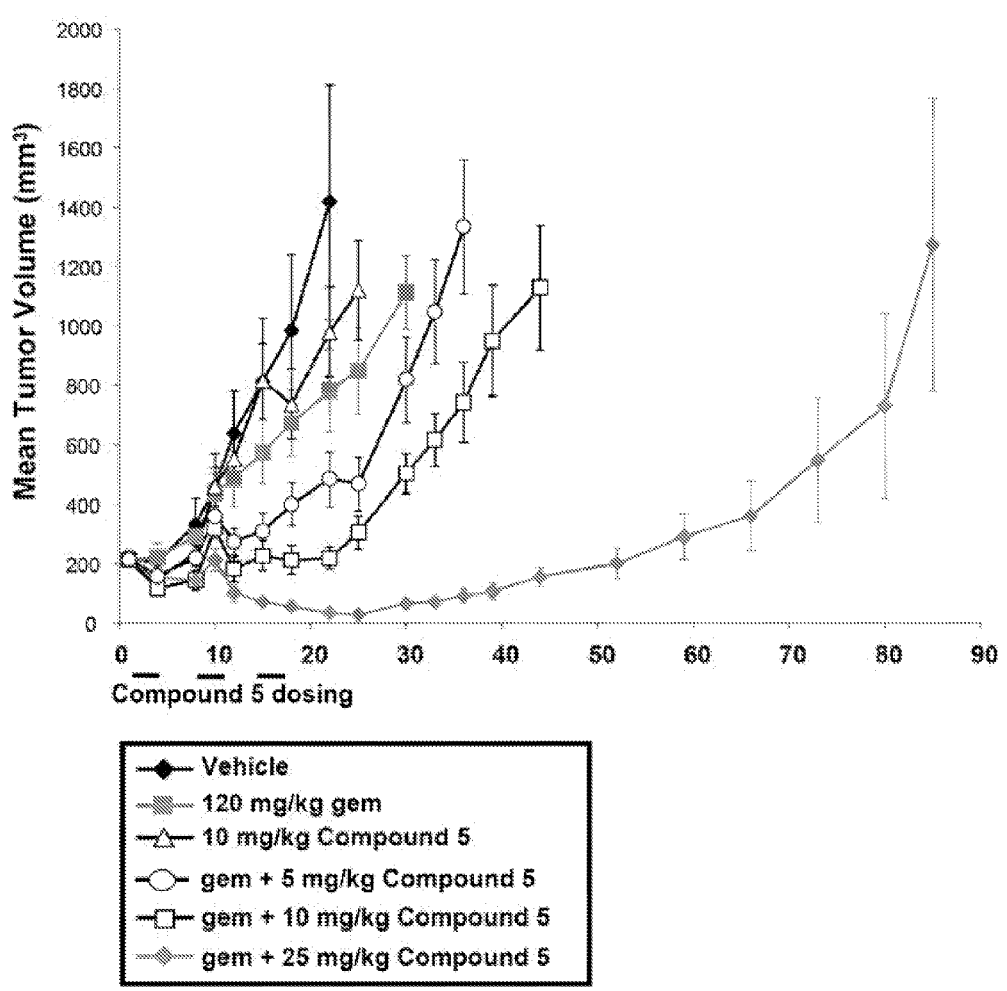
FIG. 10 shows a TGI experiment in nude mice with subcutaneous HT-29 xenografts.

Compound 5 Shows Dose Related Inhibition of Tumor Growth in Combination with Gemcitabine Female nude mice were inoculated subcutaneously with 5×10⁶ HT-29 tumor cells in 1×PBS (100 μl). Fourteen days later, mice were randomized into groups of 7 with an average tumor volume in each group of approximately 200 mm³ Sorted animals were administered gemcitabine (120 mg/kg; IP) on a Q7D×3 cycles schedule. Compound 5 (5, 10 or 25 mg/kg; PO, BID) administration was initiated 24 hours post gemcitabine and endured for 3 days as indicated. Tumor size and animal body weight were measured over the course of the study on the days indicated with data points in FIG. 10. Tumor volume was calculated using the formula: volume=(width²×length)/2. No mortalities occurred over the course of this study. Results are shown in FIG. 10, while tumor growth metrics and tolerability results are shown in the Table 5:

TABLE 5

| Treatment | Growth Delay (Days) | % Regression | Maximum % Body Weight Loss |
|---|---|---|---|
| Vehicle | N/A | 4.2 | 2.3, Day 18 |
| Gemcitabine | 11.5 | N/A | 4.9, Day 12 |
| Compound 5 (10 mg/kg) | 5.7 | 31.6 | 1.8, Day 15 |

TABLE 5-continued

| Treatment | Growth Delay (Days) | % Regression | Maximum % Body Weight Loss |
|---|---|---|---|
| Gemcitabine + Compound 5 (5 mg/kg) | 12.6 | 27.1 | 2.8, Day 18 |
| Gemcitabine + Compound 5 (10 mg/kg) | 19.8 | 45.4 | 0 |
| Gemcitabine + Compound 5 (25 mg/kg) | 59.4 | 86.7 | 2.3, Day 14 |

Example 10

Figure 11:
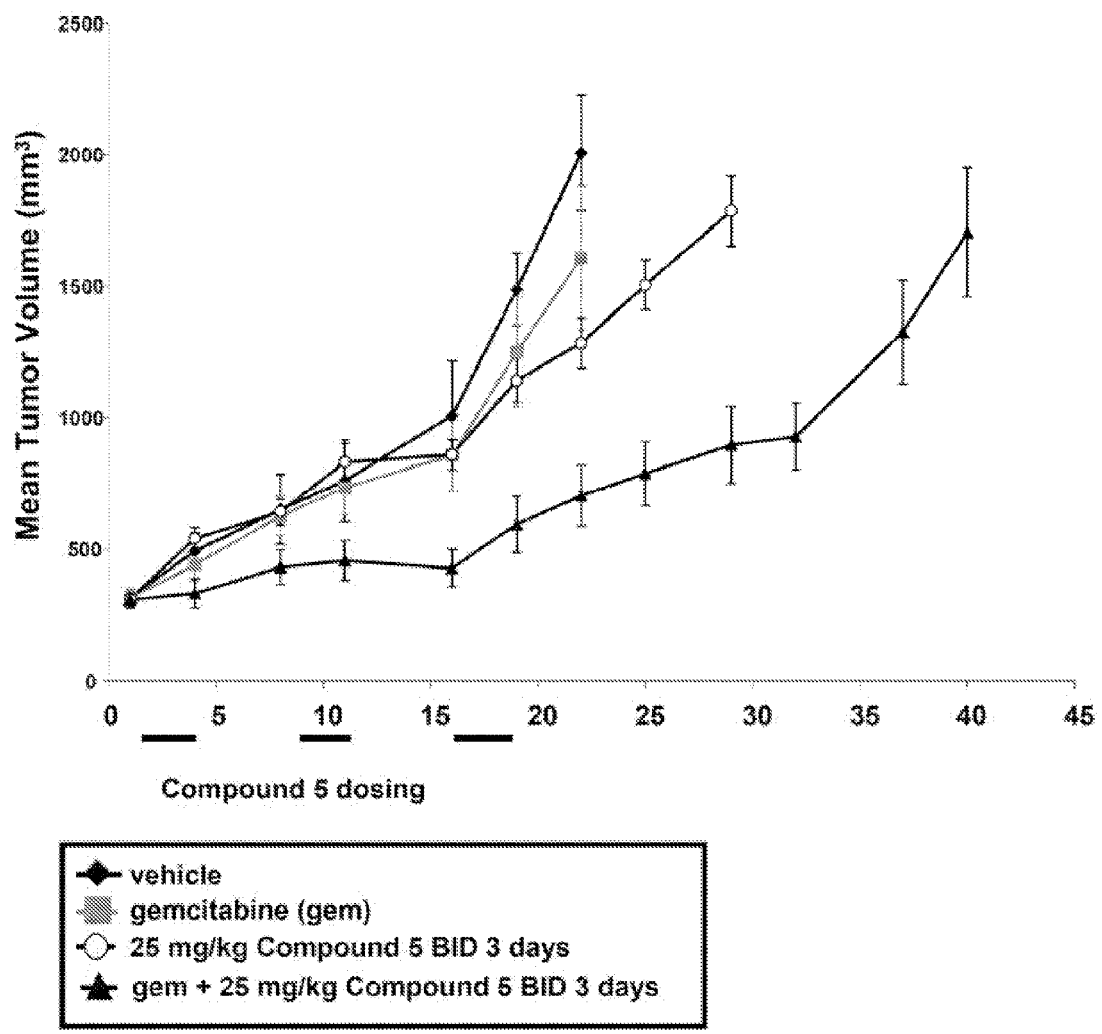
FIG. 11 shows a TGI experiment in nude mice with subcutaneous MiaPaCa2 xenografts.

Compound 5 Inhibits Tumor Growth in Combination with Gemcitabine in MiaPaCa2 Pancreatic Carcinoma Xenografts Female nude mice were inoculated subcutaneously with $7\times10^6$ MiaPaCa2 tumor cells in a 1:1 1×PBS and matrigel suspension (100 μL). Fifteen days later, mice were randomized into groups of 7 with an average tumor volume in each group of approximately 315 mm$^3$. Sorted animals were administered gemcitabine (120 mg/kg; IP) on a Q7D×3 cycles schedule. Compound 5 (25 mg/kg; PO, BID) administration was initiated 24 hours post gemcitabine and endured for 3 days as indicated. Tumor size and animal body weight were measured over the course of the study on the days indicated with data points in FIG. 11. Tumor volume was calculated using the formula: volume=(width$^2$×length)/2. No mortalities occurred over the course of this study. Results are shown in FIG. 11, while tumor growth metrics and tolerability results are shown in the Table 6:

TABLE 6

| Treatment | Growth Delay (Days) | % Tumor Growth Inhibition | Maximum % Body Weight Loss |
|---|---|---|---|
| Vehicle | N/A | N/A | 1.8, Day 4 |
| Gemcitabine | 2.2 | 6.6 | 1.5, Day 4 |
| Compound 5 (10 mg/kg) | 6.1 | 25.5 | 0.3, Day 4 |
| Gemcitabine + Compound 5 (25 mg/kg) | 18.3 | 59.1 | 2.1, Day 16 |

Example 11

Compound 2 Shows Dose Related Inhibition of Tumor Growth in Combination with CPT-11

Figure 12:
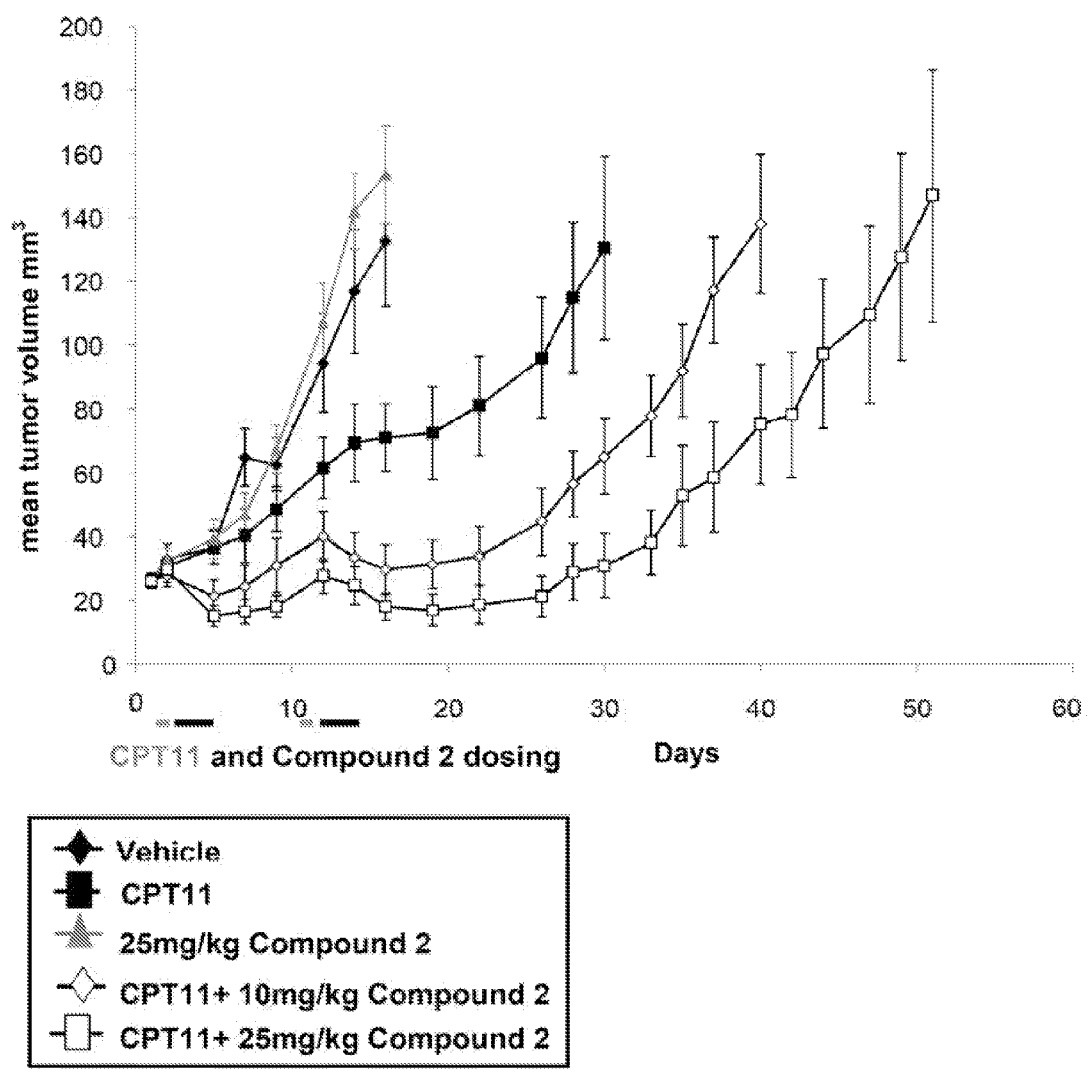
FIG. 12 shows a TGI experiment in nude mice with subcutaneous HT-29 xenografts.

Female nude mice were inoculated subcutaneously with $5\times10^6$ HT-29 tumor cells in 1×PBS (100 μL). Fourteen days later, mice were randomized into groups of 8 with an average tumor volume in each group of approximately 260 mm$^3$. Sorted animals were administered CPT11 (100 mg/kg; IP) on a Q10D×2 cycles schedule. Compound 2 (10 or 25 mg/kg; PO, BID) administration was initiated 24 hours post CPT11 and endured for 3 days as indicated. Tumor size and animal body weight were measured over the course of the study on the days indicated with data points in FIG. 12. Tumor volume was calculated using the formula: volume=(width$^2$×length)/2. No mortalities occurred over the course of this study. Results are shown in FIG. 12, while tumor growth metrics and tolerability results are shown in Table 7:

TABLE 7

| Treatment | Growth Delay (Days) | % Regression | Maximum % Body Weight Loss |
|---|---|---|---|
| Vehicle | N/A | N/A | N/A |
| CPT11 | 14.2 | N/A | 0.08 |
| Compound 2 | N/A | N/A | N/A |
| Combination 10 mg/kg | 23 | 18.3 | 1.4 |
| Combination 25 mg/kg | 33.3 | 41.6 | 9.1 |

Example 12

Compound 5 Shows Dose Related Inhibition of Tumor Growth in Combination with CPT-11

Figure 13:
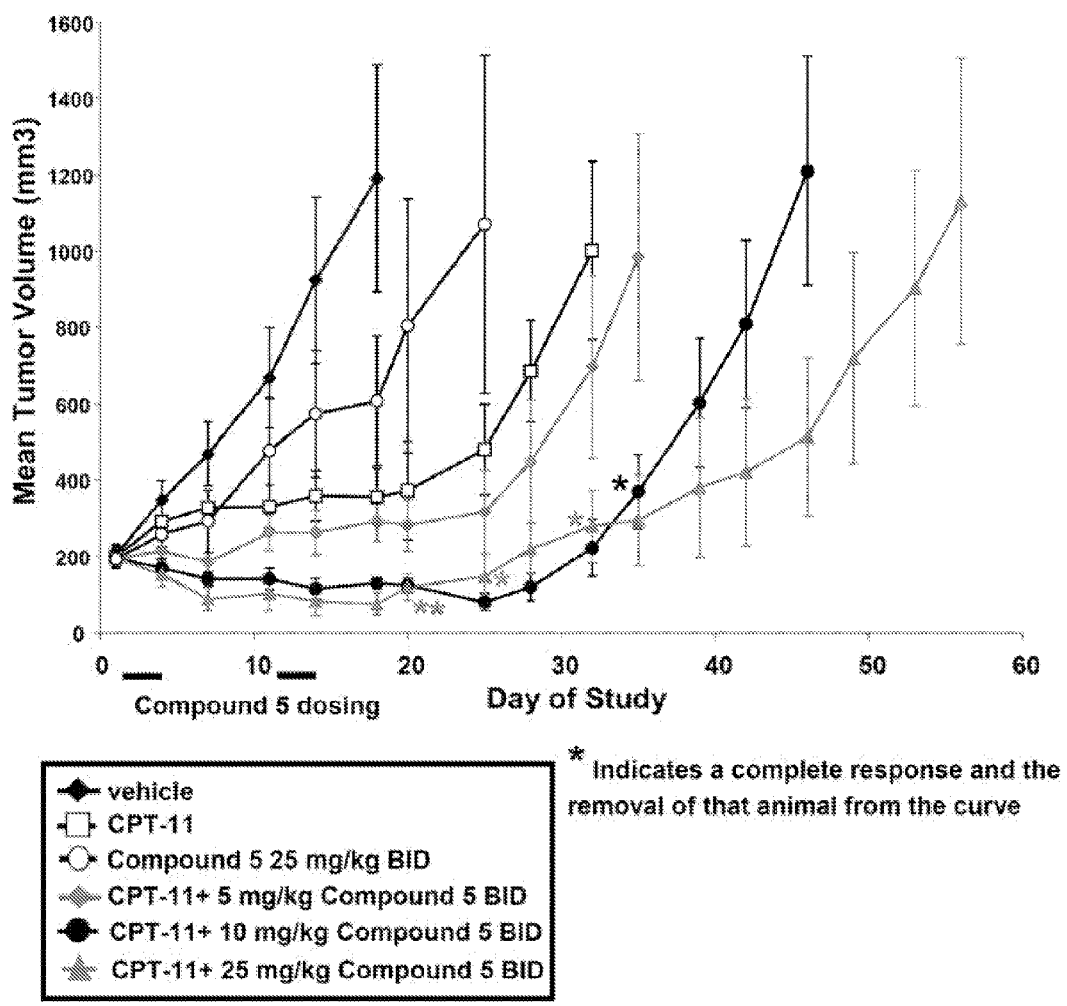
FIG. 13 shows a TGI experiment in nude mice with subcutaneous HT-29 xenografts.

Female nude mice were inoculated subcutaneously with $4\times10^6$ HT-29 tumor cells in 1×PBS (100 μL). Twelve days later, mice were randomized into groups of 7 with an average tumor volume in each group of approximately 200 mm$^3$. Sorted animals were administered CPT11 (100 mg/kg; IP) on a Q10D×2 cycles schedule. Compound 5 (5, 10, or 25 mg/kg; PO, BID) administration was initiated 24 hours post CPT11 and endured for 3 days as indicated. Tumor size and animal body weight were measured over the course of the study on the days indicated with data points in FIG. 13. Tumor volume was calculated using the formula: volume=(width$^2$×length)/2. No mortalities occurred over the course of this study. Results are shown in FIG. 13, while tumor growth metrics and tolerability results are shown in Table 8:

TABLE 8

| Treatment | Growth Delay (Days) | % Regression | Maximum % Body Weight Loss |
|---|---|---|---|
| Vehicle | N/A | N/A | N/A |
| CPT11 | 16.6 | N/A | 6.3, Day 18 |
| Compound 5 | 7.7 | N/A | 2.5, Day 18 |
| Combination 5 mg/kg | 19.5 | 4.5 | 4.8, Day 18 |
| Combination 10 mg/kg | 28.3 | 59.3 | 4.4, Day 7 |
| Combination 25 mg/kg | 38.5 | 61 | 10.0, Day 18 |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed:

1. A method for treating cancer comprising administering a DNA damaging agent followed by four doses of a CHK1 inhibitor, wherein the first two doses of the CHK1 inhibitor are administered one day after the DNA damaging agent, and the third and fourth doses of the CHK1 inhibitor are administered two days after the DNA damaging agent, and wherein said CHK1 inhibitor is selected from the group consisting of:

(R)—N-(4-(3-aminopiperidin-1-yl)-5-bromo-1H-pyrrolo[2,3-b]pyridin-3-yl)nicotinamide; (R)—N-(4-(3-aminopiperidin-1-yl)-5-bromo-1H-pyrrolo[2,3-b]pyridin-3-yl)isobutyramide; (R)—N-(5-bromo-4-(3-(methylamino)piperidin-1-yl)-1H-pyrrolo[2,3-b]pyridin-3-yl)nicotinamide; (R)—N-(4-(3-aminopiperidin-1-yl)-5-bromo-1H-pyrrolo[2,3-b]pyridin-3-yl)-5-methylnicotinamide; (R)—N-(4-(3-aminopiperidin-1-yl)-5-bromo-1H-pyrrolo[2,3-b]pyridin-3-yl)cyclopropanecarboxamide; (R)—N-(4-(3-aminopiperidin-1-yl)-5-bromo-1H-pyrrolo[2,3-b]pyridin-3-yl)-3-methylbutanamide; and (R)—N-(4-(3-aminopiperidin-1-yl)-5-bromo-1H-pyrrolo[2,3-b]pyridin-3-yl)-2-cyclopropylacetamide.

2. The method of claim 1, wherein the CHK1 inhibitor is (R)—N-(4-(3-aminopiperidin-1-yl)-5-bromo-1H-pyrrolo[2,3-b]pyridin-3-yl)nicotinamide.

3. The method of claim 1, wherein the CHK1 inhibitor is (R)—N-(4-(3-aminopiperidin-1-yl)-5-bromo-1H-pyrrolo[2,3-b]pyridin-3-yl)isobutyramide.

4. The method of claim 1, wherein the CHK1 inhibitor is (R)—N-(5-bromo-4-(3-(methylamino)piperidin-1-yl)-1H-pyrrolo[2,3-b]pyridin-3-yl)nicotinamide.

5. The method of claim 1, wherein the CHK1 inhibitor is (R)—N-(4-(3-aminopiperidin-1-yl)-5-bromo-1H-pyrrolo[2,3-b]pyridin-3-yl)-5-methylnicotinamide.

6. The method of claim 1, wherein the CHK1 inhibitor is (R)—N-(4-(3-aminopiperidin-1-yl)-5-bromo-1H-pyrrolo[2,3-b]pyridin-3-yl)cyclopropanecarboxamide.

7. The method of claim 1, wherein the CHK1 inhibitor is (R)—N-(4-(3-aminopiperidin-1-yl)-5-bromo-1H-pyrrolo[2,3-b]pyridin-3-yl)-3-methylbutanamide.

8. The method of claim 1, wherein the CHK1 inhibitor is (R)—N-(4-(3-aminopiperidin-1-yl)-5-bromo-1H-pyrrolo[2,3-b]pyridin-3-yl)-2-cyclopropylacetamide.

9. The method of claim 1, wherein the doses of the CHK1 inhibitor are administered between the biologically effective dose and the maximum tolerated dose.

10. The method of claim 1, wherein the DNA damaging agent is selected from the group consisting of gemcitabine, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, pemetrexed, and radiation.

11. The method of claim 1, wherein the DNA damaging agent is selected from the group consisting of gemcitabine, irinotecan, temozolomide, capecitabine, camptothecin, cisplatin, ara-C, and 5-FU.

12. The method of claim 1, wherein the DNA damaging agent is selected from the group consisting of gemcitabine, irinotecan, temozolomide and capecitabine.

13. The method of claim 1, wherein the DNA damaging agent is selected from the group consisting of gemcitabine, irinotecan, cisplatin, oxaliplatin, carboplatin and cytarabine.

14. The method of claim 1, wherein the DNA damaging agent is selected from the group consisting of gemcitabine and irinotecan.

15. A method for treating cancer comprising administering a DNA damaging agent followed by six doses of a CHK1 inhibitor, wherein the first two doses of the CHK1 inhibitor are administered one day after the DNA damaging agent, the third and fourth doses of the CHK1 inhibitor are administered two days after the DNA damaging agent, and the fifth and sixth dose of the CHK1 inhibitor are administered three days after the DNA damaging agent, and wherein said CHK1 inhibitor is selected from the group consisting of: (R)—N-(4-(3-aminopiperidin-1-yl)-5-bromo-1H-pyrrolo[2,3-b]pyridin-3-yl)nicotinamide; (R)—N-(4-(3-aminopiperidin-1-yl)-5-bromo-1H-pyrrolo[2,3-b]pyridin-3-yl)isobutyramide; (R)—N-(5-bromo-4-(3-(methylamino)piperidin-1-yl)-1H-pyrrolo[2,3-b]pyridin-3-yl)nicotinamide; (R)—N-(4-(3-aminopiperidin-1-yl)-5-bromo-1H-pyrrolo[2,3-b]pyridin-3-yl)-5-methylnicotinamide; (R)—N-(4-(3-aminopiperidin-1-yl)-5-bromo-1H-pyrrolo[2,3-b]pyridin-3-yl)cyclopropanecarboxamide; (R)—N-(4-(3-aminopiperidin-1-yl)-5-bromo-1H-pyrrolo[2,3-b]pyridin-3-yl)-3-methylbutanamide; and (R)—N-(4-(3-aminopiperidin-1-yl)-5-bromo-1H-pyrrolo[2,3-b]pyridin-3-yl)-2-cyclopropylacetamide.

16. The method of claim 15, wherein the CHK1 inhibitor is (R)—N-(4-(3-aminopiperidin-1-yl)-5-bromo-1H-pyrrolo[2,3-b]pyridin-3-yl)nicotinamide.

17. The method of claim 15, wherein the CHK1 inhibitor is (R)—N-(4-(3-aminopiperidin-1-yl)-5-bromo-1H-pyrrolo[2,3-b]pyridin-3-yl)isobutyramide.

18. The method of claim 15, wherein the CHK1 inhibitor is (R)—N-(5-bromo-4-(3-(methylamino)piperidin-1-yl)-1H-pyrrolo[2,3-b]pyridin-3-yl)nicotinamide.

19. The method of claim 15, wherein the CHK1 inhibitor is (R)—N-(4-(3-aminopiperidin-1-yl)-5-bromo-1H-pyrrolo[2,3-b]pyridin-3-yl)-5-methylnicotinamide.

20. The method of claim 15, wherein the CHK1 inhibitor is (R)—N-(4-(3-aminopiperidin-1-yl)-5-bromo-1H-pyrrolo[2,3-b]pyridin-3-yl)cyclopropanecarboxamide.

21. The method of claim 15, wherein the CHK1 inhibitor is (R)—N-(4-(3-aminopiperidin-1-yl)-5-bromo-1H-pyrrolo[2,3-b]pyridin-3-yl)-3-methylbutanamide.

22. The method of claim 15, wherein the CHK1 inhibitor is (R)—N-(4-(3-aminopiperidin-1-yl)-5-bromo-1H-pyrrolo[2,3-b]pyridin-3-yl)-2-cyclopropylacetamide.

23. The method of claim 15, wherein the doses of the CHK1 inhibitor are administered between the biologically effective dose and the maximum tolerated dose.

24. The method of claim 15, wherein the DNA damaging agent is selected from the group consisting of gemcitabine, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, pemetrexed, and radiation.

25. The method of claim 15, wherein the DNA damaging agent is selected from the group consisting of gemcitabine, irinotecan, temozolomide, capecitabine, camptothecin, cisplatin, ara-C, and 5-FU.

26. The method of claim 15, wherein the DNA damaging agent is selected from the group consisting of gemcitabine, irinotecan, temozolomide and capecitabine.

27. The method of claim 15, wherein the DNA damaging agent is selected from the group consisting of gemcitabine, irinotecan, cisplatin, oxaliplatin, carboplatin and cytarabine.

28. The method of claim 15, wherein the DNA damaging agent is selected from the group consisting of gemcitabine and irinotecan.

* * * * *